United States Patent [19]

Bieniarz et al.

[11] Patent Number: 5,191,066

[45] Date of Patent: Mar. 2, 1993

[54] SITE-SPECIFIC CONJUGATION OF IMMUNOGLOBULINS AND DETECTABLE LABELS

[75] Inventors: Christopher Bieniarz, Highland Park; Mazhar Husain, Libertyville; Howard E. Bond, Lake Forest, all of Ill.

[73] Assignee: Abbott Laboratories, Abbott Park, Ill.

[21] Appl. No.: 624,169

[22] Filed: Dec. 7, 1990

[51] Int. Cl.[5] .................... C07K 15/12; C07K 15/28
[52] U.S. Cl. ........................ 530/391.1; 530/391.3; 530/391.5; 530/391.7; 530/391.9
[58] Field of Search .............. 530/390, 391.1, 391.3, 530/391.5, 391.7, 391.9; 424/85.91

[56] References Cited

U.S. PATENT DOCUMENTS

| | | | |
|---|---|---|---|
| 4,140,679 | 2/1979 | Malley | 530/390 |
| 4,232,119 | 11/1980 | Carlsson et al. | 530/390 |
| 4,340,535 | 7/1982 | Voisin et al. | 530/391.9 |
| 4,699,784 | 10/1987 | Shiu et al. | 424/85.91 |
| 4,981,953 | 1/1991 | Barbieri et al. | 530/390 |
| 4,994,385 | 2/1991 | Bieniarz et al. | 530/390 |

OTHER PUBLICATIONS

O'Shannessy et al., "Labeling of the Oligosaccharide Moieties of Immunoglobulins", *J. Immunol. Methods*, 1987, vol. 99, pp. 153-161.

*Primary Examiner*—Jeffrey E. Russel
*Attorney, Agent, or Firm*—Daniel W. Collins; Thomas M. Breininger; Lawrence S. Pope

[57] ABSTRACT

A process for producing a derivatized immunoglobulin and conjugates prepared therewith are provided. The derivatized immunoglobulin is produced by introducing sulfhydryl groups in the Fc region of an immunoglobulin wherein the Fab portion of the immunoglobulin is not altered. The derivatized immunoglobulin is used to prepare conjugates with various detectable moieties wherein a controlled distance exists between the Fc region of the immunoglobulin and the detectable moiety. The conjugates are particularly useful for performing immunoassays, and exhibit improved longevity, specificity and sensitivity.

19 Claims, 5 Drawing Sheets

|—————| |—————| |—————|
1:250 (2:1)   1:500 (2:1)   1:1000 (2:1)

|—————| |—————| |—————|
1:2000 (2:1)   1:4000 (2:1)   1:8000 (2:1)

1:16,000 (2:1)

CONTROL
1:3000

SITE-SPECIFIC CONJUGATION OF IMMUNOGLOBULINS AND DETECTABLE LABELS

FIELD OF THE INVENTION

This invention relates to site-specific conjugation of immunoglobulins and detectable labels without alteration of the complementarity defined region of such immunoglobulins, and methods for preparing such conjugates. In particular, the present invention relates to the conjugation of immunoglobulins and detectable labels at specific sites on the immunoglobulin while, at the same time, maintaining the accessibility of analyte binding sites on the immunoglobulin.

BACKGROUND OF THE INVENTION

Although a variety of methods have been described for preparing conjugates of immunoglobulins and detectable labels, such as antibody-enzyme conjugates, such methods have resulted in random conjugation at many sites leading to heterogeneity and lack of reproducibility in the conjugates.

Site-specific carbohydrate labeling of the Fc region of antibodies with enzymes has also been described in O'Shannessy, et al., "Labeling of the Oligosaccharide Moieties of Immunoglobulins", *Journal of Immunological Methods*, Vol. 99 (1987) (pages 153-161). However, conjugates prepared according to such method result in distances between the enzyme and the antibody which are intrinsically short, leading to distorted, conformationally strained antibodies and/or enzymes.

European Patent Application No. 32,863 describes conjugation methods and conjugation agents for linking compounds containing carbohydrate moieties or carboxyl groups to compounds containing thiol moieties or electron-deficient moieties. In particular, the coupling of immunoglobulins at the Fc region to labels, such as enzymes, is described. However, such methods and linking reagents used thereby provide reaction conditions whereby there is essentially no discrimination between the disulfides on the Fc region and the complementarity defined region of the immunoglobulin. This lack of discrimination results in alteration of the complementarity defined region by reduction of disulfide bonds therein to thereby affect the binding sites on the immunoglobulin.

Accordingly, there is a need for a technique to prepare site-specific conjugates which avoids reductive cleavage of the disulfide bonds in, and deterioration of, the complementarity defined region of the antibody.

SUMMARY OF THE INVENTION

According to the present invention, sulfhydryl groups introduced in the Fc region of immunoglobulins are coupled to enzymes wherein the Fab portion of the immunoglobulin is not altered, and a controlled distance exists between the Fc region and the enzyme label. As a result, the conjugates prepared according to the present invention exhibit greater binding capacity and signal generating ability than those conjugates prepared according to methods previously described. The disadvantages generated by short, distorted and/or conformationally strained conjugates are thus avoided, while at the same time, improved conjugate longevity, specificity, sensitivity, and other performance factors result therefrom.

In particular, the sulfhydryl group is introduced through the Fc glycosylated portion of the immunoglobulin through a linking group containing a -NH-structure wherein the Fab portion, or complementarity defined region, is not altered. A presently preferred class of such substituted or derivatized immunoglobulin molecules is characterized by the formula:

$$mY(X-R_1-SH)_n \quad (1)$$

wherein:
m is an integer from 1 through 20;
Y is an immunoglobulin molecule, wherein the Fc glycosylated region is reactive with a linker; and wherein either:

X can be —CH$_2$NH— or

(i)

R$_1$ is a linking group containing 1 through 20 carbon atoms; and
n is an integer from 1 through 20; or
(ii) X—R$_1$—SH of formula (1) can be reduced glutathione or reduced hydrazidolipoamide.

The derivatized immunoglobulin molecule is readily coupled through its terminal sulfhydryl group to various detectable moieties, and the resulting conjugates are useful in a variety of diagnostic and therapeutic applications.

The detectable moieties which can be coupled to such a derivatized antibody (immunoglobulin) molecule are themselves first derivatized so as to contain sulfhydryl-reactive functional groups which are preferably positioned as terminal groups, in a sterically unimpaired position, on the detectable moiety. Examples of such reactive functional groups include haloacetates and preferably, maleimides. Techniques known in the art may be employed for preparing such derivatized moieties, and for preparing such conjugates. Preferably, conjugates according to the present invention comprise the derivatized molecules described above conjugated with an enzyme. The enzyme includes a coupling group, such as maleimide, haloacetyl (e.g., iodoacetyl, bromoacetyl and chloroacetyl), at the end of a long linking group. These conjugates are particularly useful in enzyme immunoassays.

Preferred conjugates contain a bifunctional coupling group of the structure:

(2)

wherein:
X and R$_1$ are as defined in Formula (1); and
L is a linking group containing 1 through 40 carbon atoms, wherein L can be the same as or different than R$_1$.

In Formula (2), X is joined to a moiety (Y) as defined in Formula (1) and L is joined to a detectable moiety (E).

More preferably, the class of such conjugates can be expressed by the formula:

wherein:
X is selected from the group consisting of —CH$_2$NH—, —CH=NNHC—, a fragment of reduced glutathione, and a fragment of reduced hydrazidolipoamide;

R$_1$ is a group containing 1 through 20 carbon atoms;

R$_2$ is cyclohexylmethyl;

R$_3$ is an alkylene group containing 1 through 10 carbon atoms; and k is an integer of 1 through 10.

A presently preferred class of conjugates is characterized by the formula:

wherein:
Q is the heterobifunctional coupling group of Formula (3);

Y is as defined in Formula (1);

E is a detectable moiety;

n is as defined in Formula (1); and o and p are each an independently selected integer of 1 through 10.

Preferably, in Formula (4), the ratio of o to p is in the range of from between about 1:1 to about 1:10, and n is in the range of from between about 1 to about 10. Conjugates of Formula (4) display improved homogeneity and lower polydispersity, and surprisingly improved sensitivity compared to conjugates prepared according to methods known in the art.

A derivatized immunoglobulin of the present invention is prepared by the sequential steps of site-specific periodate oxidation of immunoglobulin followed by reductive amination with an appropriate polyaminodisulfide reagent, and then disulfide reduction.

BRIEF DESCRIPTION OF THE DRAWINGS

FIG. 4 illustrates the comparison of the activity of a goat anti-human IgE/alkaline phosphatase conjugate prepared according to the present invention with a goat anti-human IgE/alkaline phosphatase conjugate prepared according to a method known in the art.

DESCRIPTION OF THE INVENTION (a) Definitions

As used herein, the term "immunoglobulin" refers to a member of the class of protein molecules present, for example, in plasma, colostrum, tears, and other body fluids. An immunoglobulin, or antibody, combines specifically, non-covalently, and reversibly, with antigens.

The term "antibody" is used herein to refer to a homogeneous or heterogeneous population of immunoglobulins (such as monoclonal antibodies or polyclonal antiserum). An antibody-antigen complexation occurs by contact between specific combining sites of an immunoglobulin, known as complementarity defined regions, and antigenic determinants.

Five immunoglobulin classes are distinguished, identified as IgA, IgD, IgE, IgG and IgM. IgG is the predominant immunoglobulin in plasma, comprising about 75% of total plasma immunoglobulin, and is the most abundant immunoglobulin of internal body fluids, particularly extravascular materials, for combatting microorganisms and their toxins. There are four subclasses of IgG, identified as IgG-1, IgG-2, IgG-3 and IgG-4, which are distinguished by differences in amino acid sequences. In human serum, IgG-1 comprises about 65% of plasma immunoglobulins.

As used herein, the term "Fc region" means the region of an immunoglobulin that corresponds to the stem or leg of the Y-shaped immunoglobulin molecule, and consists of the C-terminal sections of the two heavy chains linked by one or more disulfide bonds.

As used herein, the term "Fab region" means the region of an immunoglobulin other than the Fc region. Each Fab region consists of a light chain linked by a disulfide bond to the N-terminal part of a heavy chain, wherein each such Fab region is one of the two arms of the Y-shaped immunoglobulin molecule. Each Fab region contains a single combining site in the highly variable region thereof, and behaves as a non-precipitating univalent antibody.

As used herein, the term "label" or "detectable moiety" refers to a compound which can be used to label an immunoglobulin, usually by coupling such a compound with an immunoglobulin as in a conjugate. Labels can vary greatly in structure and function and include, but are not intended to be limited to, enzymes, radiolabels, fluorogens, biotin, toxins, drugs, haptens, DNA, RNA, polysaccharides, polypeptides, liposomes, chromophores, chemiluminescers, colored particles and colored microparticles, and the like.

In the R$_1$ and R$_2$ group as defined above, for example, in Formulas (1), (2), and (3), alkyl groups are preferred, cyclohexylmethyl being a particularly preferred R$_2$ group. The term "alkyl" includes straight and branched chains when three or more carbon atoms are present. Preferred alkyl chains contain less than seven carbon atoms each. Presently most preferred are ethyl and glutathione, wherein $R_2$ is preferably cyclohexylmethyl.

(b) Derivatized immunoglobulin

A derivatized immunoglobulin of this invention is prepared by the steps of:

(i) site-specific oxidation of the immunoglobulin to convert at least two hydroxyl groups in the glycosylated zone of the Fc region of the immunoglobulin to at least two aldehyde groups;

(ii) reductive alkylation of the aldehyde groups to introduce disulfide moieties onto the Fc region of the immunoglobulin; and (iii) reduction of the disulfide groups to sulfhydryl groups, wherein aqueous liquid phase reaction conditions are employed in each step.

It is to be understood that oxidation of the immunoglobulin molecule can be accomplished by either chemical oxidation or enzymatic oxidation. For example, chemical oxidants include, but are not intended to be limited to periodate, bromine, and the like, and enzymatic oxidants include, but are not intended to be limited to, the sequential use of neuraminidase and galactose oxidase, and the like.

Similarly, reduction of the disulfide groups of the immunoglobulin to generate terminal sulfhydryl groups can be accomplished by either chemically or enzymatically cleaving the disulfide groups. For example, the chemical reduction of disulfide groups in the Fc introduced linkers may be accomplished by the use of mercaptoethanol, dithiothreitol (DTT), sodium borohydride, sodium dithionite, and the like. In the case of enzymatic reduction of disulfide groups at the Fc site, such reduction may be accomplished by exposing certain chemically introduced linkers containing the disulfide bonds to the appropriate enzymes which catalytically reduce the disulfides to thiols. Thus, the oxidized form of a linker-extended glutathione could generate thiols upon exposure to glutathione reductase. Similarly, the oxidized form of linker-extended lipoamide could generate thiols upon exposure to lipoamide dehydrogenase.

When the reductive alkylation is carried out with an amino disulfide compound, a Schiff base is formed which is stabilized by reduction.

After each of the indicated steps, the modified immunoglobulin product is preferably purified and concentrated according to methods known in the art.

According to the present invention, an alkali metal periodate, such as sodium periodate ($NaIO_4$), is employed to specifically oxidize vicinal diol moieties in a saccharide to aldehyde groups (see, for example, O'Shannessy et al.). The glycosylated zone of the Fc region of the immunoglobulin thereby undergoes a site-specific oxidation of at least two hydroxyl groups therein to two aldehyde groups. Accordingly, the complementarity defined region undergoes essentially no structural alteration. As will be understood by one skilled in the art, such oxidation is dependent on a number of variables including the concentrations of the immunoglobulin reactant and of the periodate oxidizing agent, pH, temperature and time. Various combinations of such variables may, of course, also be employed.

Some control of the extent of oxidation appears to be accomplished by varying the number of aldehyde groups generated and ultimately the degree of labeling of the oxidized immunoglobulin. The number of aldehyde groups generated for each immunoglobulin molecule is dependent upon the oxidation conditions with more severe oxidation conditions generally producing more aldehyde groups per molecule. Preferably, the immunoglobulin contains from between about 2 to about 10 aldehyde groups for each oxidized immunoglobulin molecule in the glycosylated zone of the Fc region of the immunoglobulin.

The resulting aldehyde group-containing immunoglobulin is next most preferably purified and concentrated. Purification is preferably accomplished by chromatography. For example, one presently preferred procedure is to pass the reaction medium containing the modified immunoglobulin through a gel filtration column such as a SEPHADEX® G-25 column (Pharmacia LKB Biotechnology, Inc., Piscataway, N.J., USA) for purposes of separating the modified immunoglobulin. A column of such a composition is conventionally equilibrated and eluted using a buffer, such as sodium phosphate and sodium chloride having a pH of preferably about 7.0. During elution, fractions are collected, and fractions having a suitable predetermined absorbance peak (e.g., 280 nm) are pooled. Protein concentration can be calculated from the absorbance peak using a suitable extinction coefficient.

Concentration of the aldehyde group-containing immunoglobulin from such a pool can be conveniently and preferably accomplished. A present preference is to employ centrifugation at about 5000 X g using tubes containing a molecular weight sizing membrane, such as Centricon® tubes (Amicon Corp, Danvers, Mass., USA) having the capacity to pass a material having a number average molecular weight cut-off of about 30,000.

Next, the purified, concentrated aldehyde group containing immunoglobulin is contacted under aqueous liquid phase conditions with an appropriate aminodisulfide reagent or a dihydrazido disulfide reagent to introduce at least one disulfide group for each immunoglobulin through the aldehyde groups.

Although it is possible to employ an amino or hydrazido substituted thiol (i.e. sulfhydryl) terminated compound, disulfide compounds are particularly preferred over thiol terminated compounds in order to maximize yields of the desired thiol-terminated group substituent, and to avoid undesired side reactions.

Accordingly, one preferred class of such disulfide compounds for use in reacting with an aldehyde group-containing immunoglobulin can be oxidized glutathione, hydrazidolipoamide, or a compound characterized by the formula:

$$X-R_1-S-S-R_1-X \qquad (5)$$

where:

X is selected from the group consisting of $-CH_2NH_2$ and and $R_1$ is a group containing 1 through 20 carbon atoms, preferably methylene.

As would be understood by one skilled in the art, the addition of bifunctional reagents to an ensemble of molecules causes both intramolecular modifications to the molecules and intermolecular modifications to the molecules. Accordingly, the aforementioned disulfide compounds of the present invention may similarly react with the carbohydrate-rich Fc regions of the immunoglobulin to result in either a large heterocyclic ring on the Fc region containing the disulfide bonds when reacting intramolecularly, or may introduce a disulfide group between two immunoglobulins when reacting intermolecularly.

When the reaction with each aldehyde group on the immunoglobulin results in the formation of a Schiff base, the base may to be stabilized by reduction. For example, when reacted with a diamine disulfide reagent, stabilization by reduction of the Schiff base is required, whereas when the coupling reagent is dihydrazide disulfide, stabilization by reduction is not required. Such reductive stabilization is conveniently accomplished with an alkali metal cyanoborohydride, preferably sodium cyanoborohydride, under controlled reaction conditions. A present preference is to add the cyanoborohydride to the reaction medium within a time interval of from between about 5 minutes to about 24 hours after the addition of diaminodisulfide, more preferably from between about 15 minutes to about 60 minutes after such addition of diaminodisulfide. The reduction of the Schiff base results in the formation of a divalent secondary amine group.

The resulting derivatized disulfide group-containing immunoglobulin is preferably purified and concentrated according to the procedure and equipment described for use in the purification and concentration of the oxidized, aldehyde group-containing immunoglobulin.

Next, the purified, concentrated disulfide group-containing immunoglobulin is contacted under aqueous liquid phase conditions with a reducing agent which reduces the disulfide groups thereof to free sulfhydryl terminated groups. Where a chemical reducing agent is employed, a dithiol, such as dithiothreitol, is preferred. Where an enzymatic reducing reagent is employed, glutathione reductase, lipoamide dehydrogenase, and the like, are preferred. The reduction of disulfide groups is achieved with essentially no effect upon other portions of the immunoglobulin molecule including the disulfide groups present in the internal structure thereof. This reduction is dependent on a number of variables, including the concentration of the dithiol reducing agent, as well as the pH, wherein combinations of disulfide reducing conditions can be employed. In this regard, the present inventors have surprisingly and unexpectedly found that at low enough concentrations of a reducing agent, such as dithiothreitol, (e.g., about 2 mM), only the disulfide bonds introduced by the present method into the Fc region undergo reduction, with the concomitant generation of thiols, wherein the disulfide bonds in the complementarity defined region and the hinge region are essentially unaffected at such low concentration of the reducing agent. Although an aldehyde group of the Fc region will react irreversibly with amine-containing linkers (e.g., cystamine and oxidized glutathione) only in the presence of sodium cyanoborohydride as a reducing reagent, sodium cyanoborohydride is not necessary when the linkers to be reacted with aldehydes of the Fc region contain a hydrazido group Notably, use of sodium cyanoborohydride for reductive amination of the aldehydes on the Fc region does not reduce disulfide bonds in the reactive linkers or in the interchain links of the immunoglobulin.

According to the present invention, a substantially complete conversion of the Fc introduced disulfide side chain groups to sulfhydryl terminated side chains is accomplished. In contrast, reduction of the disulfide groups as previously described above (European Patent Application No. 32,863) occurs at substantially higher concentrations of the chemical reducing agent.

The resulting sulfhydryl group containing immunoglobulin is preferably purified. A present preference is to utilize a purification procedure and equipment such as hereinabove described for use in the preparation of the oxidized, aldehyde group-containing immunoglobulin.

The purified product is directly suitable for conjugation with a detectable moiety.

(c) Conjugates of Derivatized Immunoglobulin With Detectable Moieties

A Fc site-specifically derivatized sulfhydryl group-containing immunoglobulin of the present invention can be conjugated with essentially any protein or other type of detectable moiety or label known in the art to produce new and useful conjugates. Such detectable moieties or labels include, but are not intended to be limited to, enzymes, chromogens, luminescent, phosphorescent compounds, chemiluminescent compounds, fluorescent compounds, and the like. The sulfhydryl terminated side chain permits production of conjugates wherein the unconjugated or normal activity of the starting immunoglobulin and the label are retained, and by employing the derivatized immunoglobulin of the present invention, conjugates are produced wherein constraints on conformational freedom are avoided so that increased performance and stability can be achieved.

A label that is used for coupling with a derivatized immunoglobulin of the present invention is derivatized so as to contain at least one terminal sulfhydryl reactive functional group. Examples of such reactive functional groups include, but are not intended to be limited to, maleimide, haloacetyl groups such as iodoacetyl, bromoacetyl and chloroacetyl, and the like. Techniques known in the art may be used for preparing such derivatized markers and for preparing such conjugates.

As described above, preferred conjugates of the present invention are those comprising an Fc site-specifically derivatized sulfhydryl group-containing immunoglobulin molecule coupled with a derivatized enzyme having a side chain coupling group that is terminated by a maleimide functional group. The coupling group employed in the enzyme is preferably chosen so as not to restrict the conformational freedom of the enzyme or its function after conjugating. In the coupling reaction, the terminal sulfhydryl group of the derivatized immunoglobulin molecule reacts with the terminal maleimide group of the derivatized enzyme to form the conjugate.

As would be understood by one skilled in the art, the present invention contemplates many different conjugates made with a coupling group as described herein. Many molecules of a single detectable moiety molecule can be attached to a single derivatized immunoglobulin molecule of this invention, or many derivatized immunoglobulin molecules can be attached to a single detectable moiety molecule. Also, a single conjugate of coupled molecules can contain a plurality of bifunctional coupling groups (Q) as described.

In preparing the preferred conjugates of the present invention, derivatized enzymes which have been made using the techniques described in copending U.S. patent application Ser. No. 246,971, filed Sep. 22, 1988, entitled "Heterobifunctional Coupling Agents", now U.S. Pat. No. 4,994,385, and incorporated herein by reference, can be used. Such preferred starting enzymes are characterized by the formula:

(7)

wherein:

$R_2$ is a group containing 1 through 20 carbon atoms;
$R_3$ is an alkylene group containing 1 through 10 carbon atoms;
k is an integer from 1 through 10;
n is an integer from 1 through 20; and
E is an enzyme.

In the derivatized enzymes of Formula (7), the linking group between the enzyme (E) and the terminal maleimide group preferably contains a relatively long oligomeric chain of amino acids, from between about 2 and about 4 amino acids, which not only provides better physical separation between conjugated molecules incorporating such a linking group, but also functions to enhance the water solubility and dispersibility of a conjugate containing such chain.

To prepare a conjugate of a derivatized immunoglobulin of this invention and a derivatized enzyme having a side chain terminated by a maleimide group, any convenient procedure known in the art can be used. For example, a purified sulfhydryl group-containing immunoglobulin molecule is admixed under aqueous liquid phase conditions with a purified enzyme having a maleimide terminated side chain. Various combinations of reaction conditions may be employed in the coupling reaction of the sulfhydryl group with the maleimide group. The coupling reaction is preferably carried out in the dark and is allowed to proceed for at least about 1 hour, preferably for about 12 hours. It is to be understood that periods of more than about 20 hours normally do not appear to increase the yield of conjugate. The conjugation or coupling reaction is believed to go substantially to completion based on starting molar ratios of reactant groups.

It is preferred to produce a conjugate having no remaining free or reactive sulfhydryl groups. Accordingly, the unreacted sulfhydryl groups on the derivatized immunoglobulin molecules in the conjugate are reacted with a capping agent, such as maleimides substituted with alkyl groups of methyl through heptyl. A preferred capping agent is N-ethyl maleimide (NEM). One convenient and presently preferred capping procedure is to add, to a buffered aqueous product conjugate-containing medium, an aqueous solution of NEM to a final concentration of about 0.3 mM, and agitate the mixture for at least about one hour at ambient temperatures. The capped conjugate can be used directly for immunoassay purposes.

The conjugates according to the present invention are useful for the determination of an analyte in homogeneous and heterogeneous immunoassay systems known in the art, such as competitive immunoassays, sandwich immunoassays, immunometric immunoassays, and the like, where the amount of a detectable moiety employed therein can be measured and correlated to the amount of analyte present in a test sample. Generally, such measurement depends upon the ability of an immunoglobulin, i.e., an antibody, to bind to a specific analyte wherein a conjugate comprising an antibody to such analyte labeled with a detectable moiety is employed to determine the extent of such binding. Typically, the extent of binding is determined by the amount of the detectable moiety present in the conjugate which either has or has not participated in a binding reaction with the analyte, wherein the amount of the detectable moiety detected and measured can be correlated to the amount of analyte present in the test sample.

The conjugates according to the present invention are presented in a commercially packaged form as a composition or admixture where the compatibility of the reagents will allow or as a test kit, i.e., a packaged combination of one or more containers holding a conjugate according to the present invention and other appropriate reagents for performing an immunoassay as described herein and as known in the art. The reagents can further include other materials as are known to be useful in the assay from a user standpoint, such as buffers, diluents, standards, controls, and the like.

The present invention will now be illustrated, but is not intended to be limited, by the following examples:

EXAMPLE 1

Site-specific Thiolation of Anti-Carcinoembryonic Antigen (Anti-CEA) Immunoglobulins and Its Coupling to Calf Intestinal Alkaline Phosphatase (a) Introduction of Thiol Groups in the Fc region of the Antibody A 1 mL solution of anti-CEA immunoglobulins (3–4 mg/mL in 0.1 M triethanolamine (TEA) buffer containing 0.16 M sodium chloride, pH 8) was placed in an amber vial. A 110 uL solution of 200 mM sodium-m-periodate (Sigma Chemical Co., St. Louis, Mo., USA) dissolved in 0.1 M TEA buffer, pH 8, containing 0.16 M NaCl was added to the antibody solution and the resulting mixture was gently stirred on a rotary agitator for 1 hour at approximately 5° C. in the dark.

The oxidized antibody was purified from the above reaction mixture by chromatography on a 1×45 cm column of Sephadex G-25. The column was equilibrated and eluted with 0.1 M sodium phosphate, pH 7.0, containing 0.1 M NaCl. Fractions of about 1 mL each were collected during elution and the absorbance at 280 nm was determined. The peak fractions were pooled and the protein concentration of the immunoglobulins pool was calculated from its absorbance at 280 nm using an extinction coefficient ($E_{1cm}^{1\%}$) of 13.9.

The immunoglobulins pool was concentrated to 1.0 mL by centrifuging at 5000 x g using Centricon tubes (Amicon, Danvers, Mass., USA) which contain a membrane sized to pass material having a number average molecular weight of up to about 30,000. The concentrate was admixed with 250 uL of 0.75 M cystamine dihydrochloride (Sigma Chemical Co.) dissolved in 0.1 M sodium phosphate, pH 7.0, containing 0.1 M NaCl, and the resulting mixture was gently stirred at room temperature. After about 15 minutes, 63 uL of 0.3 mM sodium cyanoborohydride (Sigma Chemical Co.) dissolved in 0.1 M sodium phosphate, pH 7.0, containing 0.1 M sodium chloride, was added and the resulting mixture was gently stirred on a rotary agitator overnight at room temperature.

The derivatized antibody was recovered by gel filtration on a 1×45 cm column of Sephadex G-25. The column was equilibrated and eluted with 0.1 M sodium phosphate, pH 7.0, containing 0.1 M NaCl and 2 mM EDTA (ethylene diamine tetraacetic acid). Fractions of about 1 mL each were collected during elution and the absorbance at 280 nm was determined. The peak fractions were pooled and the concentration of the modified antibody was calculated from its absorbance at 280 nm as indicated above.

The pooled antibody was concentrated again, employing Centricon tubes of the same size and source as described above, to 1 mL and treated with 50 μL of 40 mM dithiothreitol (Sigma Chemical Co.; dissolved in 0.1 M sodium phosphate, pH 7.0, containing 0.1 M NaCl and 2 mM EDTA) for 15 minutes at room temperature. The excess of dithiothreitol was removed by chromatography on a 1×45 cm Sephadex G-25 column. Fractions of about 1.0 mL each were collected and absorbance at 280 nm was measured. The peak fractions with absorbance at 280 nm of 0.3 or higher were pooled and stored on ice until the start of conjugation.

b) Derivatization of Enzyme [A 0.6 mL aliquot of calf intestinal alkaline phosphatase (Boehringer Mannheim, Indianapolis, Ind., USA) at 10 mg/mL was diafiltered against 0.1 M sodium phosphate buffer, pH 7.0, containing 0.1 M NaCl, 1 mM $MgCl_2$, and 0.1 mM $ZnCl_2$. The volume was made up to 1 mL with the dialysis buffer and the enzyme solution was placed into a vial. To the enzyme solution was added 200 μL of DMF containing 0.8 mg of succinimidyl (tricaproamido cyclohexylmethyl) N-maleimide (STCM) linker, a 30-atom extended heterobifunctional linker reagent with succinimide ester and maleimide termini, prepared as described in European Patent Application Publication No. 0314127 and incorporated herein by reference. The resulting reaction mixture was gently stirred on a rotary agitator for 30 minutes at room temperature and the derivatized enzyme was purified by chromatography on a 1×45 cm column of Sephadex G-25. The column was equilibrated and eluted with 0.1 M sodium phosphate buffer, pH 7.0, containing 0.1 M NaCl, 1 mM $MgCl_2$ and 0.1 mM $ZnCl_2$. Fractions of about 1 mL each were collected during elution and the absorbance at 280 nm was determined. The peak fractions were pooled and the concentration of the enzyme in the pool was calculated from its absorbance at 280 nm using an extinction coefficient $(E_{1cm}^{1\%})$ of 10.

c) Conjugation of Derivatized Enzyme with Antibody Thiolated at the Fc region

The derivatized alkaline phosphatase from step (b) above was combined with the activated antibody from step (a) above in a molar ratio of 2:1 (enzyme to antibody). The mixture was gently stirred overnight at 2°–8° C. on a rotary agitator which resulted in approximately 90% conjugation of the starting enzyme and antibody as indicated by HPLC and SDS-PAGE evaluations.

The unreacted thiol groups on the antibody were capped by treatment with N-ethylmaleimide (NEM; Sigma Chemical Co.) for a period of 1 hour at room temperature. Aliquots of a 5 mM solution were added to the conjugate so that the final concentration of NEM in the conjugate was about 0.3 mM.

d) Performance of the Fc Conjugate

The performance of the Fc conjugate prepared as described above was evaluated by a sandwich-type microparticle capture enzyme immunoassay (MEIA) for carcinoembryonic antigen [CEA](King, et al., In Immunodiagnosis of Cancer, 2nd Ed., in press) using the Abbott IMx ® System (Abbott Laboratories, Abbott Park, Ill., U.S.A.; (Fiore, et al., Clin. Chem., Volume 34, pages 1726–1732, 1988). According to this assay format, latex microparticles covalently coupled with capture antibody (anti-CEA) were incubated first with sample containing known or unknown amounts of analyte (CEA) and then with alkaline phosphatase-labelled antibody conjugate (anti-CEA/alkaline phosphatase conjugate). Unadsorbed materials were removed at each step by capillary action and buffer washes. Following the removal of unbound conjugate, enzyme substrate (4-methyl umbelliferyl phosphate) was added and rate of fluorescence increase was measured.

Figure 1:
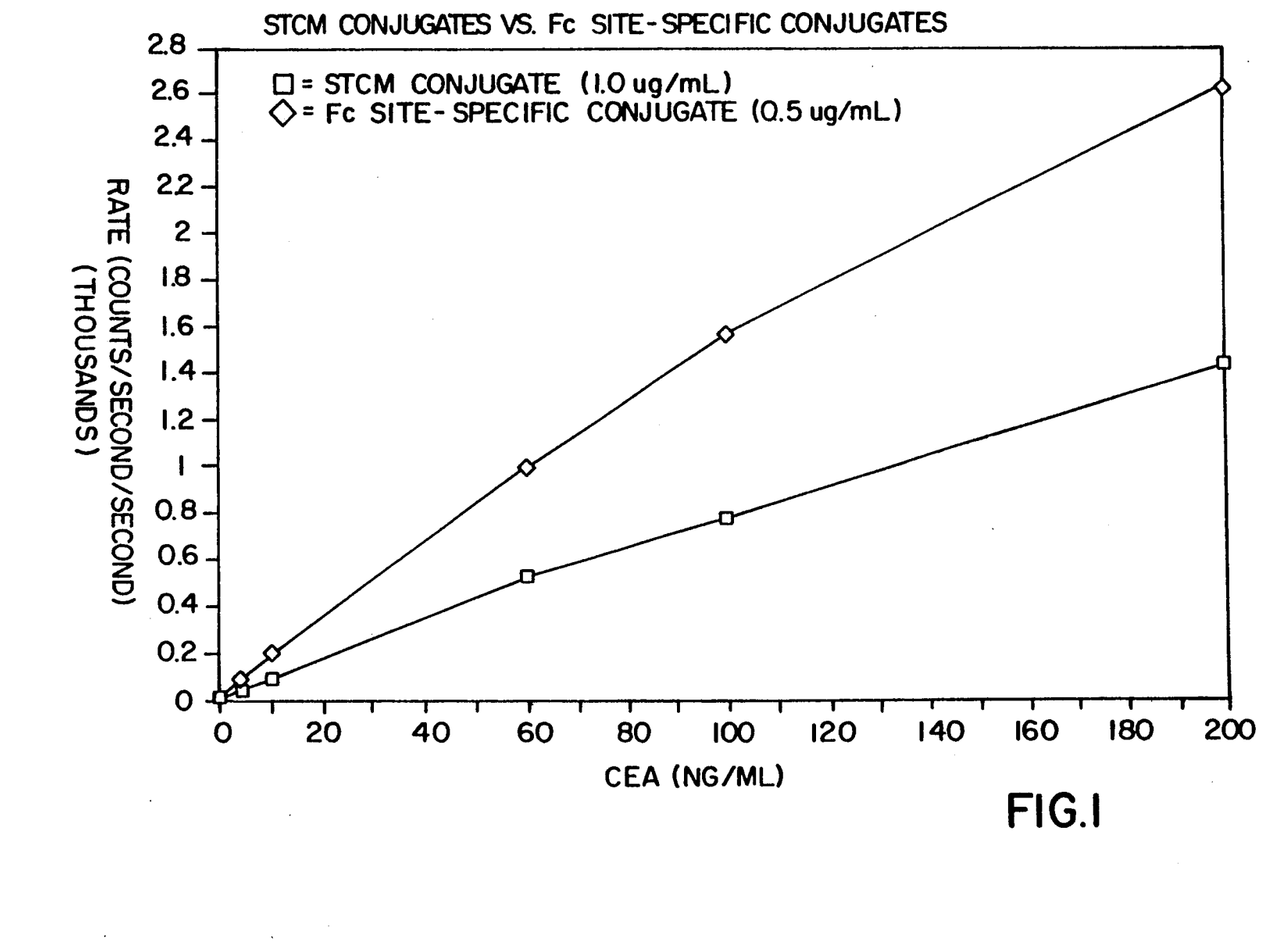
FIG. 1 illustrates the comparison of the activity of a carcinoembryonic antigen (CEA)/alkaline phosphatase conjugate prepared according to the present invention with an anti-CEA/alkaline phosphatase conjugate prepared according to a conjugation method known in the art.

The data in FIG. 1 and Table 1 compare the performance of the Fc site-specific conjugate of the present invention with that of an anti-CEA/alkaline phosphatase conjugate prepared by combining iminothiolane-activated enzyme with STCM linker-activated antibody (STCM conjugate) as described in European Patent Application Publication No. 0314127. The results clearly demonstrate a 400% improvement in assay sensitivity with the Fc site-specific conjugate of the present invention over the STCM conjugate.

TABLE 1

Comparison of Anti-CEA/Alkaline Phosphatase Fc Site-Specific Conjugates with Conjugate prepared using Iminothiolane/STCM Extended Linker (STCM Conjugate) in IMx CEA Assay

| CEA Standards (ng/mL) | Rate of Fluorescence (Counts/s/s) | |
|---|---|---|
| | STCM Conjugate (1 ug/mL) | Fc Conjugate (0.5 ug/mL) |
| 0 | 9.0 | 19.1 |
| 4 | 46.3 | 94.9 |
| 10 | 97.4 | 200.6 |
| 60 | 534.1 | 1000.3 |
| 100 | 785.1 | 1565.7 |
| 200 | 1433.1 | 2634.3 |

The two conjugates described above were also each identically stressed for 3 days at 45° C to evaluate their stability. The data presented in Table 2 show that thermal stability of the Fc site-specific conjugate of the present invention was comparable to that of the STCM conjugate previously described, and that even after heat stress, the Fc site-specific conjugate of the present invention gave more than a 3-fold higher signal compared to the STCM conjugate.

TABLE 2

Comparison of Anti-CEA/Alkaline Phosphatase Fc Site-Specific Conjugate with STCM Conjugate after Heat Stress (3 Days at 45° C.)

| CEA Standards (ng/mL) | Rate of Fluorescence (Counts/s/s) | |
|---|---|---|
| | STCM Conjugate (1 ug/mL) | Fc Conjugate (0.5 ug/mL) |
| 0 | 12.7 | 26.1 |
| 4 | 37.6 | 66.2 |
| 10 | 79.2 | 132.6 |
| 60 | 377.9 | 616.3 |
| 100 | 599.1 | 968.3 |
| 200 | 1050.9 | 1669.6 |

EXAMPLE 2

Fc Site-Specific Thiolation of Anti-Cancer Antigen (CA) 19-9 Immunoglobulins and Its Coupling To Calf Intestinal Alkaline Phosphatase An anti-CA 19-9 IgG and calf intestinal alkaline phosphatase were each activated essentially as described in steps (a) and (b), respectively, of Example 1, and then were conjugated by combining them in a molar ratio of 1.5:1 (enzyme to antibody). The unreacted thiols were capped with N-ethylmaleimide as described in Example 1.

Figure 2:
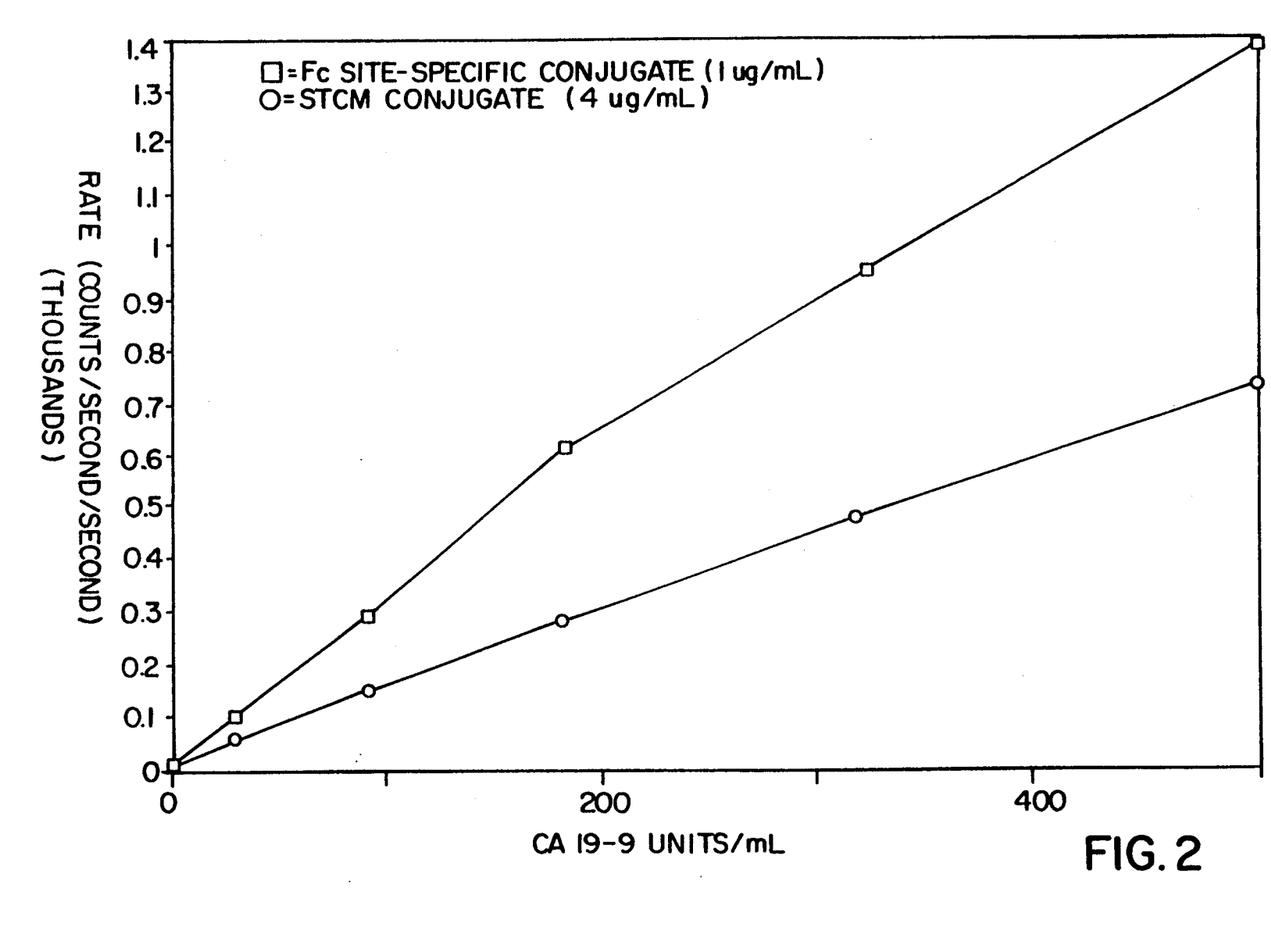
FIG. 2 illustrates the comparison of the activity of an anti-cancer antigen (CA) 19-9/alkaline phosphatase conjugate prepared according to the present invention with an anti-CA 19-9/alkaline phosphatase conjugate prepared according to a conjugation method known in the art.

The performance of the Fc site-specific conjugate was analyzed using a sandwich-type MEIA format employing the Abbott IMx system and compared to the performance of the STCM conjugate prepared as described in Example 1. The results presented in FIG. 2 and Table 3 demonstrate approximately 8-fold higher sensitivity for the Fc site-specific conjugate over the STCM conjugate.

TABLE 3

Comparison of Anti-CA 19-9/Alkaline Phosphatase Fc Site-Specific Conjugate with STCM Conjugates

| CA 19-9 Standards (Units/mL) | Rate of Fluorescence (Counts/s/s) | |
|---|---|---|
| | STCM Conjugate (4 ug/mL) | Fc Conjugate (1 ug/mL) |
| 0 | 5.0 | 18.4 |
| 30 | 60.7 | 75.2 |
| 90 | 141.1 | 237.8 |
| 180 | 276.0 | 462.7 |
| 320 | 462.1 | 750.5 |
| 500 | 732.0 | 1072.2 |

EXAMPLE 3

Fc Site-Specific Thiolation of Anti-Urinary Tract Infections (UTI) Immunoglobulins and Its Coupling To Calf Intestinal Alkaline Phosphatase Rabbit and sheep anti-UTI immunoglobulins and calf intestinal alkaline phosphatase were activated essentially as described in steps (a) and (b), respectively, of Example 1, and then conjugated by combining the derivatized materials at a molar ratio of 2:1 (enzyme to antibody), and incubating overnight at 2°-8° C. with a gentle shaking on a rotary agitator. Following overnight incubation, residual thiol groups in the conjugates were capped with 5 mM N-ethylmaleimide as described in Example 1.

The performance of such Fc conjugates was evaluated by Abbott Test-Pack TM immunoassay device [Abbott Laboratories, Abbott Park, Ill., USA; W. E. Brown III, Clin. Chem., Volume 33, page 1567, (1987)] using E. Coli extract as the test organism and compared to that of a periodate conjugate prepared according to the method of Nakane and Kawaoi (P. K. Nakane and Akira Kawaoi, J. Histochem. and Cytochem, Volume 22, pages 1084–1091, 1974). The Fc site-specific conjugates were found to be about 4-fold more active than the periodate conjugate.

EXAMPLE 4

Fc Site-Specific Thiolation of Anti-Biotin Immunoglobulins and Its Coupling To Calf Intestinal Alkaline Phosphatase Rabbit anti-biotin immunoglobulins and calf intestinal alkaline phosphatase were activated essentially as described in steps (a) and (b), respectively, in Example 1, and then were conjugated by combining the derivatized materials in a 1:1 molar ratio. The resulting mixture was gently stirred overnight at 2°-8° C. on a rotary agitator. The following morning, unreacted thiols in the resulting conjugate were capped with 5 mM stock solution of NEM as described in Example 1.

Figure 3:
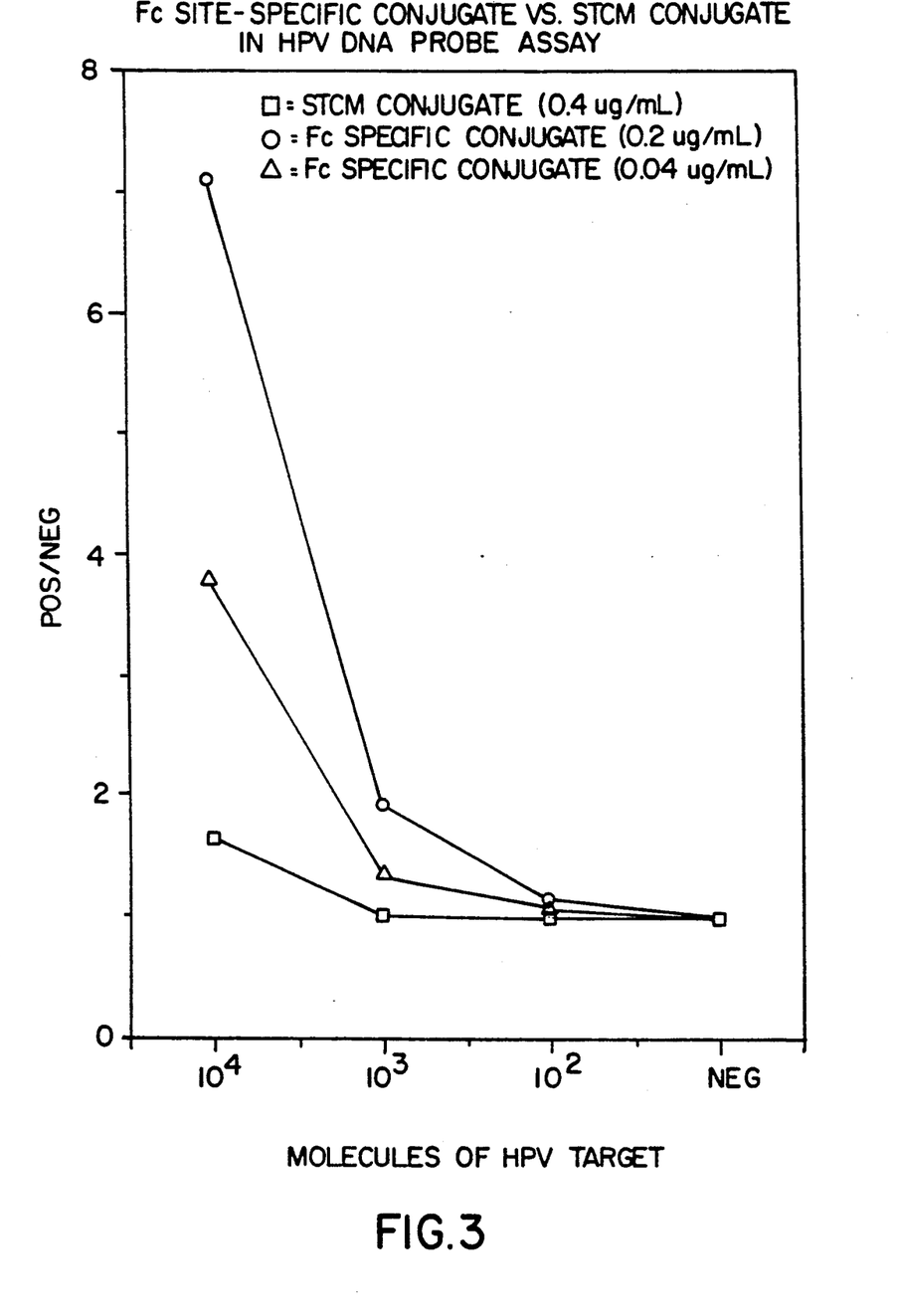
FIG. 3 illustrates the comparison of the activity of an anti-biotin/alkaline phosphatase conjugate prepared according to the present invention with an anti-biotin/alkaline phosphatase conjugate prepared according to a conjugation method known in the art.

The Fc site-specific conjugate when evaluated by DNA Probe Human Papilloma Virus (HPV) assay showed a 20-fold increase in sensitivity compared to the STCM conjugate prepared as indicated in Example 1 above (see FIG. 3 and Table 4).

TABLE 4

Comparison of Anti-Biotin/Alkaline Phosphatase Fc Site-Specific Conjugate with STCM Conjugates by HPV-DNA Probe Assay

| | Signal Noise | | |
|---|---|---|---|
| Molecules of HPV Target | STCM Conjugate (0.4 ug/mL) | Fc Conjugates (0.04 ug/mL) | Fc Conjugates (0.2 ug/mL) |
| 0 | 1.0 | 1.0 | 1.0 |
| 100 | 1.0 | 1.08 | 1.17 |
| 1000 | 1.0 | 1.40 | 1.92 |
| 10000 | 1.7 | 3.83 | 7.12 |

EXAMPLE 5

Fc Site-Specific Thiolation of Anti-Cancer Antigen (CA 125) Immunoglobulins and Its Coupling To Calf Intestinal Alkaline Phosphatase Monoclonal anti-CA 125 immunoglobulins and alkaline phosphatase were activated essentially as described in steps (a) and (b) respectively, of Example 1, and then were conjugated by combining the derivatized materials in respective molar ratios of 1:1 and 2:1 (enzyme to antibody). The resulting mixtures were gently stirred overnight at 2°-8° C. on a rotary agitator. The resulting conjugates were then subjected to the end group capping procedure of Example 1 by adding 5 mM NEM.

The performance of these conjugates was evaluated using a sandwich-type MEIA format employing the Abbott IMx System and was found to be comparable to that of conjugates prepared by combining the DTT-reduced antibody with the enzyme derivatized with the STCM extended linker as described in European Patent Application Publication No. 0314127.

EXAMPLE 6

Fc Site-Specific Thiolation of Anti-Human IgM Immunoglobulins and Its Coupling To Calf Intestinal Alkaline Phosphatase Goat anti-human IgM immunoglobulins and calf intestinal alkaline phosphatase were activated essentially as described in steps (a) and (b), respectively, of Example 1 and then were conjugated by combining the derivatized materials in respective molar ratios of 1:1 and 2:1 (enzyme to antibody) and gently stirring the mixtures overnight at 2°-8° C. on a rotary agitator. The resulting conjugates were then subjected to the end group capping procedure of Example 1 by adding 5 mM NEM.

The performance of the Fc site-specific conjugates evaluated by a sandwich-type MEIA using the Abbott IMx system was found to be comparable to that of the conjugates prepared using iminothiolane and STCM extended linker as described in Example 1 above.

EXAMPLE 7

Fc Site-Specific Thiolation of Anti-Human IgE Immunoglobulins and Its Coupling To Calf Intestinal Alkaline Phosphatase Goat anti-human IgE immunoglobulins and the alkaline phosphatase were activated essentially as described in steps (a) and (b), respectively, of Example 1 and then were conjugated by combining the derivatized materials in respective molar ratio of 1:1. The antibody/enzyme mixture was gently stirred overnight at 2°–8° C. on a rotary agitator and the resulting conjugate was subjected to the end group capping procedure of Example 1 by adding 5 mM NEM.

The performance of the Fc conjugate was evaluated by a sandwich-type immunoassay as follows. A panel of allergens immobilized on a piece of nitrocellulose paper was treated with human IgE molecules specific to various allergens. The nitrocellulose paper was washed with phosphate buffer saline, treated with the Fc site-specific conjugates at various dilutions ranging from 1:1000 to 1:16000 following by color reaction for alkaline phosphatase. The results shown in FIG. 4 demonstrate that Fc site-specific conjugate is about 3-times more sensitive compared to the conjugates prepared by the periodate method of Nakane and Kawaoi referred to above.

EXAMPLE 8

Site specific Thiolation of Anti-Pituitary Thread Protein (Anti-PTP) and Its Coupling To Calf Intestinal Alkaline Phosphatase Anti-PTP immunoglobulins and the alkaline phosphatase were activated essentially as described in steps (a) and (b), respectively, of Example 1 and then were conjugated in a molar ratio of 1:1 and 2:1 (enzyme to antibody). The antibody/enzyme mixture was gently stirred overnight at 2°–8° C. on a rotary agitator and the resulting conjugate was subjected to the end group capping procedure of Example 1 by adding 5 mM NEM.

Figure 5:
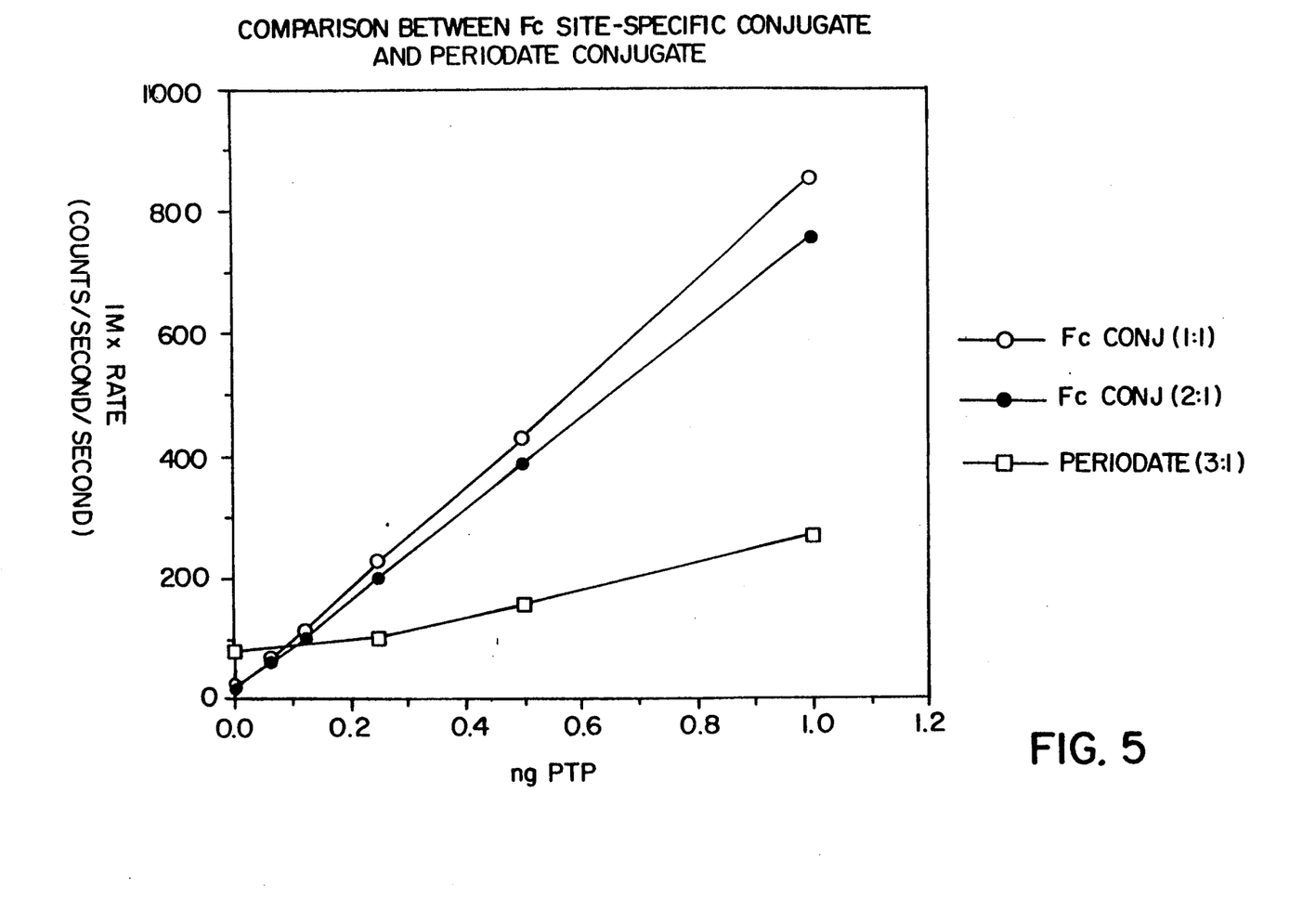
FIG. 5 illustrates the comparison of the activity of an anti-pituitary thread protein (PTP)/alkaline phosphatase conjugate prepared according to the present invention with an anti-PTP/alkaline phosphatase conjugate prepared according to a conjugation method known in the art (values in parentheses represent enzyme to antibody ratios).

The performance of the Fc site-specific conjugate was evaluated using a sandwich-type MEIA format employing the Abbott IMx System and compared to that of the periodate conjugate prepared according to the method of Nakane and Kawaoi referred to above. The results presented in FIG. 5 and Table 5 clearly show a 10-fold improvement in signal to noise ratio (S/N) of the Fc site-specific conjugate as compared to the periodate conjugate.

TABLE 5

Comparison of Anti-Pancreatic Thread Protein/Alkaline Phosphatase Fc versus Periodate Conjugate by IMx PTP Assay

| PTP (ng) | Rate of Fluorescence (Counts/s/s) | |
|---|---|---|
| | Periodate Conjugate (1 ug) | Fc Conjugate (1 ug) |
| 0.0 | 76.4 | 23.2 |
| 0.062 | N.d. | 66.3 (2.86) |
| 0.125 | N.d. | 111.9 (4.82) |
| 0.250 | 102.1 (1.34) | 227.4 (9.80) |
| 0.500 | 155.9 (2.04) | 425.5 (18.34) |
| 1.000 | 266.4 (3.49) | 850.0 (36.64) |

[The values in parentheses represent signal to noise ratios]

EXAMPLE 9

Incorporation of Extended Analogs of Oxidized Glutathione into Fc region of Antibodies and Glutathione Reductase-Catalyzed Generation of Thiols Antibodies are oxidized with sodium periodate at pH 8 and 2°–8° C. as described in Example 1 and then, after removal of excess reagent, subjected to reductive alkylation in the presence of excess of oxidized glutathione (approximately 100 mM) and sodium cyanoborohydride (15 mM). After overnight incubation at room temperature, excess of reagent is removed by gel filtration over Sephadex G-25 as described in Example 1.

The final step in the activation of antibody is carried out enzymatically. To the derivatized antibody with extended analogs of oxidized glutathione attached covalently to the Fc region, are added a few micrograms of the enzyme, glutathione reductase and excess of NADPH (approximately 1 mM), and reaction is allowed to proceed until an adequate amount of thiols (2–6 moles/mole of antibody) are generated.

Subsequent to the generation of thiols, antibody is combined with alkaline phosphatase derivatized with STCM extended linker and the resulting mixture is gently stirred overnight at 2°–8° C. as described in Example 1. Finally the conjugate is capped with NEM as described in Example 1 and dialyzed to remove excess reagents.

EXAMPLE 10

Incorporation of Hydrazido Lipoamide and Extended Analogs of Hydrazido Lipoamide into the Fc region of Antibodies and Lipoamide Dehydrogenase-Catalyzed Generation of Thiols Antibodies are oxidized with sodium periodate at pH 8 and 2°–8° C. as described in Example 1, and then, after removal of excess periodate, treated with excess of hydrazido lipoamide or extended analogs of hydrazido lipoamide (10–50 mM). After overnight incubation at room temperature, excess of reagent is removed by gel filtration over Sephadex G-25 as described in Example 1.

The final step in the activation of antibody is carried out enzymatically. To the derivatized antibody with the lipoamide moiety covalently attached to the Fc region, are added a few micrograms of lipamide dehydrogenase and excess of NADPH (approximately 1 mM) and reaction is allowed to proceed until an adequate number of thiols (2–6 moles of thiols/ mole of antibody) are generated.

Subsequent to the generation of thiols, antibody is combined with alkaline phosphatase derivatized with STCM extended linker and the resulting mixture is gently stirred overnight at 2°–8° C. as described in Example 1. Finally, conjugate is capped with NEM as described in Example 1 and dialyzed to remove excess reagents before use.

It will be apparent that many modifications and variations of the invention as herein set forth are possible without departing from the spirit and scope thereof, and that, accordingly, such limitations are imposed only as indicated by the appended claims.

We claim:

1. A process for producing a derivatized immunoglobulin, said process comprising the steps of:
    (a) site-specifically oxidizing the glycosylated zone of the Fc region of an immunoglobulin with an oxidant to convert at least two hydroxyl groups in said zone of said immunoglobulin to an aldehyde group;

(b) reacting the oxidized immunoglobulin of step (a) with a disulfide compound wherein at least one of said aldehyde groups is reductively aminated to introduce a disulfide moiety onto the Fc region of said immunoglobulin; and (c) selectively reducing the disulfide bonds of the disulfide moiety of the reacted immunoglobulin of step (b) with an amount of a reductant sufficient to convert at least one of said disulfide moieties of said immunoglobulin into two sulfhydryl groups but insufficient to reduce the disulfide bonds in the complementarity defined region and the hinge region of said immunoglobulin thereby leaving the disulfide bonds in said complementarity defined region and said hinge region essentially unaffected.

2. The process of claim 1 wherein said disulfide compound in step (b) is of the formula:

$$X-R_1-S-S-R_1-X$$

wherein

X is an aminoalkyl group or a semihydrazone group; $R_1$ is a group containing from 1 through 20 carbon atoms; and $R_1$ and X together can form with the disulfide atoms between them a macrocyclic, heterocyclic ring or interimmunoglobulin disulfide containing chain to convert at least one aldehyde group per immunoglobulin molecule to a group which contains a disulfide moiety of the formula:

$$-X-R_1-S-S-$$

wherein:

$R_1$ and X are as defined above.

3. The process of claim 1 wherein the oxidant in step (a) is a chemical oxidant.

4. The process of claim 2 wherein X is selected from the group consisting of $CH_2—NH_2$, $$O=\overset{|}{C}NHNH_2,$$

a fragment of glutathione, a fragment of reduced hydrazidolipoamide, alkyl chain modified-length extended glutathione, and alkyl chain modified-length extended hydrazidolipoamide.

5. The process of claim 3 wherein the chemical oxidant is selected from the group consisting of alkali metal periodate, iodine and bromine.

6. The process of claim 3 wherein the chemical oxidant is sodium periodate.

7. The process of claim 1 wherein the oxidant in step (a) is an enzymatic oxidant.

8. The process of claim 7 wherein said enzymatic oxidant comprises neuraminidase and galactose oxidase and the oxidation step comprises sequentially contacting said immunoglobulin with neuraminidase and galactose oxidase.

9. The process of claim 1 wherein the disulfide compound in step (b) is selected from the group consisting of cystamine, oxidized glutathione, oxidized hydrazidolipoic acid, alkyl chain modified-length extended oxidized glutathione, and alkyl chain modified-length extended oxidized hydrazidolipoic acid.

10. The process of claim 1 wherein the reductant in step (c) is a chemical reductant selected from the group consisting of mercaptoethanol, dithiothreitol, sodium borohydride and sodium dithionite.

11. The process of claim 1 wherein the reductant in step (c) is an enzymatic reductant selected from the group consisting of glutathione reductase and lipoamide dehydrogenase.

12. The process of claim 1 wherein the sulfhydryl group-containing immunoglobulin of step (c) is contacted with a detectable moiety containing a maleimide group to produce a conjugate.

13. The process of claim 12 wherein said detectable moiety is selected from the group consisting of enzymes, chromophores, fluorescent molecules, chemiluminescent molecules, phosphorescent molecules, colored particles, and luminescent molecules.

14. The process of claim 12 wherein said detectable moiety is an enzyme.

15. The process of claim 12 wherein said maleimide group is part of a linking group.

16. The process of claim 15 wherein said linking group is a heterobifunctional linking group.

17. The process of claim 1 wherein the reductant in claim 1 is present in an amount whereby essentially no disulfide bonds of the native immunoglobulin in step (a) are reduced.

18. The process of claim 17 wherein the reductant comprises form between about 1 mM and about 5 mM dithiothreitol.

19. The process of claim 14 wherein the reductant comprises about 2 mM dithiotreitol.

* * * * *

UNITED STATES PATENT AND TRADEMARK OFFICE
CERTIFICATE OF CORRECTION

PATENT NO. : 5,191,066
DATED : March 2, 1993
INVENTOR(S) : C. Bieniarz, M. Husain, H. Bond It is certified that error appears in the above-identified patent and that said Letters Patent is hereby corrected as shown below:

Col. 10, line 67:   "0.3 mM" should read:   -- 0.3 M --

Signed and Sealed this

Seventh Day of June, 1994

BRUCE LEHMAN

Attest:

Attesting Officer

Commissioner of Patents and Trademarks